US008910913B2

(12) United States Patent
Hirose (10) Patent No.: US 8,910,913 B2
(45) Date of Patent: Dec. 16, 2014

(54) SUPPORTING APPARATUS USED MEDICAL TREATMENT (71) Applicant: Olympus Medical Systems Corp., Tokyo (JP)

(72) Inventor: Kenji Hirose, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/649,813

(22) Filed: Oct. 11, 2012

(65) Prior Publication Data

US 2013/0140412 A1    Jun. 6, 2013

Related U.S. Application Data (63) Continuation of application No. PCT/JP2012/054343, filed on Feb. 23, 2012.

(30) Foreign Application Priority Data

Mar. 3, 2011  (JP) ................................. 2011-046783

(51) Int. Cl.
A47F 5/00        (2006.01)
A61B 1/00        (2006.01)
A61B 19/00       (2006.01)

(52) U.S. Cl.
CPC ............. *A61B 1/00149* (2013.01); *A61B 19/26* (2013.01); *A61B 2019/264* (2013.01); *A61B 2019/265* (2013.01); *A61B 2019/266* (2013.01)
USPC ................ 248/123.11; 248/123.2; 248/176.3; 248/585; 248/280.11; 248/281.11; 606/1; 606/130; 600/427; 600/429; 600/471; 359/382; 359/384

(58) Field of Classification Search
CPC ............. A61B 19/26; A61B 2019/264; A61B 2019/265; A61B 2019/266; A61B 2019/268
USPC ........... 248/124.1, 129, 176.1, 176.3, 220.21, 248/220.22, 274.1, 580, 585, 123.11, 123.2, 248/280.11, 281.11; 606/1, 130, 427, 429, 606/471; 359/382, 384; 600/427, 429, 471
See application file for complete search history.

(56) References Cited

U.S. PATENT DOCUMENTS 5,186,422 A * 2/1993 Nakamura ................. 248/123.2
5,818,638 A * 10/1998 Nakamura ..................... 359/384

(Continued)

FOREIGN PATENT DOCUMENTS

DE   10 2004 063 606 A1   7/2006
JP       A-7-227398        8/1995

(Continued)

OTHER PUBLICATIONS

Translation of International Preliminary Report on Patentability dated Sep. 12, 2013 from International Application No. PCT/JP2012/054343.

(Continued)

Primary Examiner — Todd M Epps
(74) Attorney, Agent, or Firm — Oliff PLC (57) ABSTRACT A supporting apparatus used for medical treatment includes a support arm in which a leading end side is coupled to a supporting unit supporting an endoscope, and a moving arm that is coupled to a base end side of the support arm, the moving arm moving the supporting unit and supporting the supporting unit in a moved position of the supporting unit. The support arm includes a leading-end-side coupling unit that is turnably coupled to the supporting unit, a base-end-side coupling unit that is disposed in coaxial with the leading-end-side coupling unit and turnably coupled to the moving arm, and an offset unit laterally offset with respect to an axis line R passing through the leading-end-side and the base-end-side coupling units. The offset unit is freely rotatable about the axis line R with respect to the supporting unit and the moving arm.

8 Claims, 10 Drawing Sheets

(56) References Cited

U.S. PATENT DOCUMENTS

| | | | |
|---|---|---|---|
| 5,825,536 A * | 10/1998 | Yasunaga et al. | 359/384 |
| 5,836,869 A | 11/1998 | Kudo et al. | |
| 6,036,637 A | 3/2000 | Kudo | |
| 6,514,239 B2 * | 2/2003 | Shimmura et al. | 606/1 |
| 7,472,872 B2 * | 1/2009 | Nakamura | 248/123.2 |
| 7,556,626 B2 * | 7/2009 | Ueda et al. | 606/1 |
| 2001/0027313 A1 | 10/2001 | Shimmura et al. | |
| 2004/0097966 A1 | 5/2004 | Nakamura | |
| 2004/0246469 A1 | 12/2004 | Hirose | |

FOREIGN PATENT DOCUMENTS

| | | |
|---|---|---|
| JP | A-7-289563 | 11/1995 |
| JP | A-8-52157 | 2/1996 |
| JP | A-8-164148 | 6/1996 |
| JP | A-9-149877 | 6/1997 |
| JP | A-10-277054 | 10/1998 |
| JP | A-11-290339 | 10/1999 |
| JP | A-2001-258903 | 9/2001 |
| JP | A-2005-13715 | 1/2005 |
| JP | A-2005-292452 | 10/2005 |
| JP | A-2005-323876 | 11/2005 |
| JP | A-2009-297236 | 12/2009 |

OTHER PUBLICATIONS

Nov. 27, 2012 Office Action issued in Japanese Patent Application No. 2012-546273 (with English-language translation).

Jun. 12, 2012 International Search Report issued in PCT/JP2012/054343 (with English-language translation).

Mar. 19, 2012 Partial International Search Report issued in PCT/JP2012/054343 (with English-language translation).

* cited by examiner

SUPPORTING APPARATUS USED MEDICAL TREATMENT

CROSS-REFERENCE TO RELATED APPLICATIONS

This application is a Continuation Application of PCT Application No. PCT/JP2012/054343, filed Feb. 23, 2012 and based upon and claiming the benefit of priority from prior Japanese Patent Application No. 2011-046783, filed Mar. 3, 2011, the entire contents of all of which are incorporated herein by reference.

BACKGROUND OF THE INVENTION

1. Field of the Invention

The present invention relates to a supporting apparatus used for medical treatment that can maintain a supported medical observation apparatus in any position.

2. Description of the Related Art

In recent years, a surgical operation is performed using an endoscope. In the operation in which the endoscope is used, a range to be cut is reduced, and a burden on a patient can be reduced. For example, Jpn. Pat. Appln. KOKAI No. 2009-297236 proposes a supporting arm apparatus in which, in a space that can be used in the operation, a support post unit is vertically provided in a base unit that is movable in an operating room, and supporting arm is attached to the a support post unit. A supporting apparatus that supports the endoscope is provided in the supporting arm apparatus. The endoscope is attached to the supporting device, and the endoscope can vertically and horizontally be moved with a light load, and supported at a desired position According to the supporting apparatus, a visual field of the endoscope is stably ensured, the endoscope can intentionally be moved with a small force in order to finely change the visual field, and the endoscope can securely be fixed to the desired position.

In addition to an operator who performs a treatment, plural support staffs, such as an assistant who assists the treatment of the operator and a scopist who manipulates the endoscope that becomes eyes of the operator, participate in the operation in which a laparoscope is used. Therefore, for example, Jpn. Pat. Appln. KOKAI No. 9-149877 proposes a supporting apparatus including a base unit that is directly attached to an operating table and a support arm that extends from the base unit.

BRIEF SUMMARY OF THE INVENTION

According to an embodiment of the present invention, there is provided an supporting apparatus used for medical treatment comprising: a pair of coupling units which is turnably provided while separated from each other by a predetermined distance on a first rotation axis, the first rotation axis defining a longitudinal axis; a turning arm unit which includes one end portion and the other end portion, the turning arm unit extending in the longitudinal direction while being laterally separated from the first rotation axis by a predetermined distance; a pair of arm units in which the pair of coupling units and one end portion and the other end portion of the turning arm unit are coupled such that the turning arm unit can turn about the first rotation axis while a predetermined interval is maintained; a moving arm unit which is coupled to one of the pair of coupling units while being turnable about the first rotation axis, the moving arm unit supporting the turning arm unit such that the turning arm unit can move vertically and horizontally; a first tilt unit which includes a leading end portion and a base end portion, the base end portion being coupled to the other of the pair of coupling units while the base end portion is turnable about the first rotation axis; a second tilt unit which is coupled to the leading end portion of the first tilt unit while being turnable about a second rotation axis having a direction different from that of the first rotation axis; and a supporting unit which is coupled to the second tilt unit while being turnable about a third rotation axis having a direction different from that of the first and second rotation axes, the supporting unit being able to support a medical observation apparatus.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
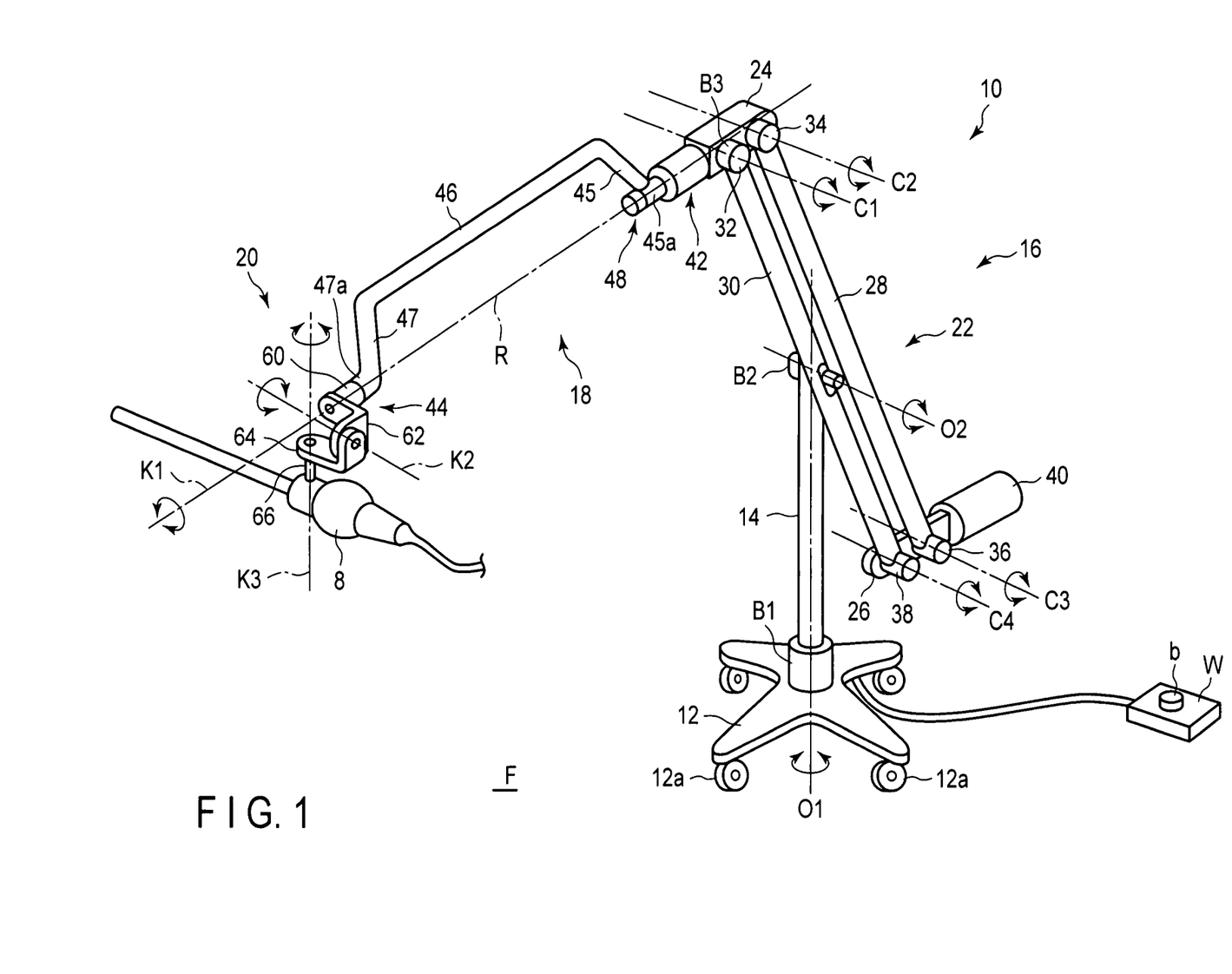
FIG. 1 is a view illustrating an entire configuration of a supporting apparatus used for medical treatment according to a first embodiment of the invention.
Figure 2:
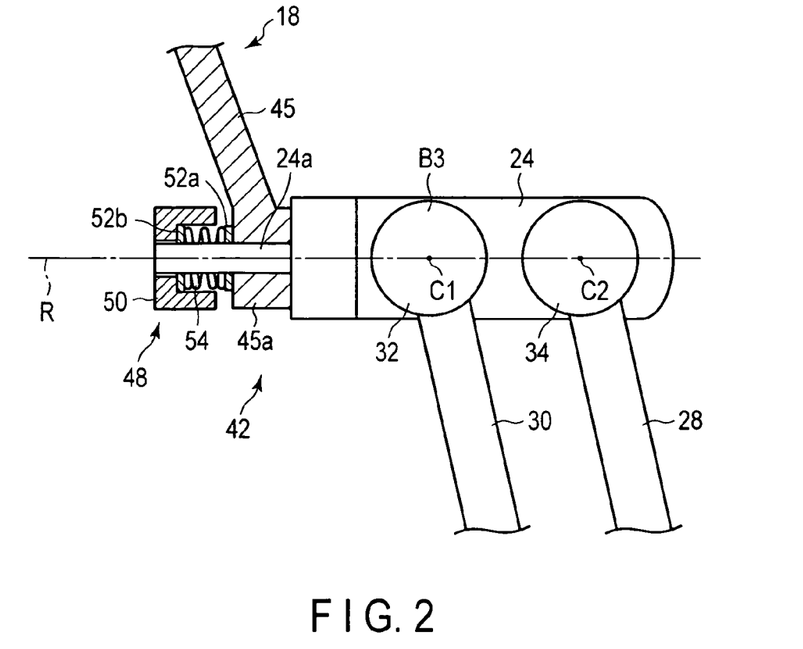
FIG. 2 is a view illustrating a detailed configuration of a coupling unit of a support arm and a moving arm of the supporting apparatus used for medical treatment in FIG. 1.
Figure 3:
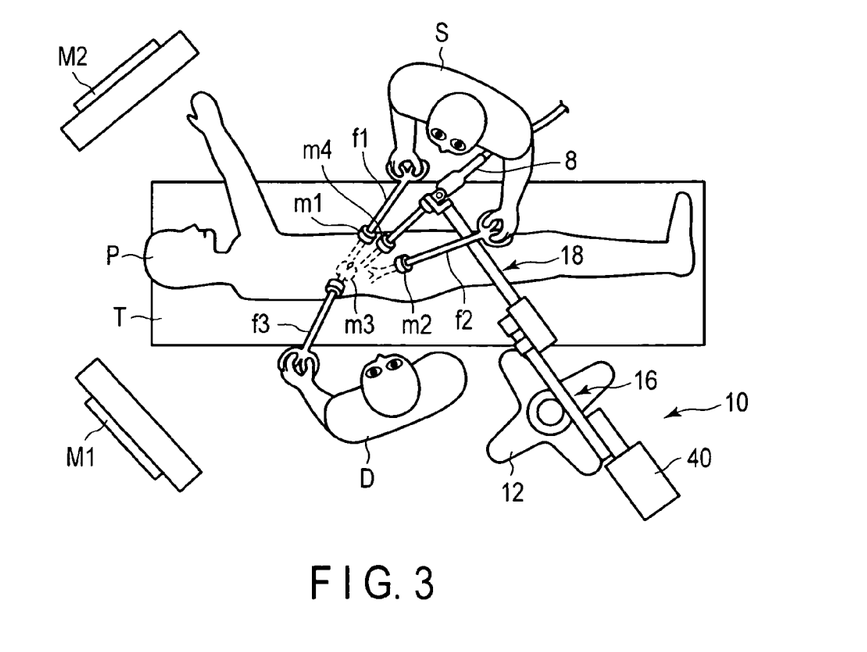
FIG. 3 is a view illustrating a situation of an operation in which the supporting apparatus used for medical treatment in FIG. 1 is used.
Figure 4:
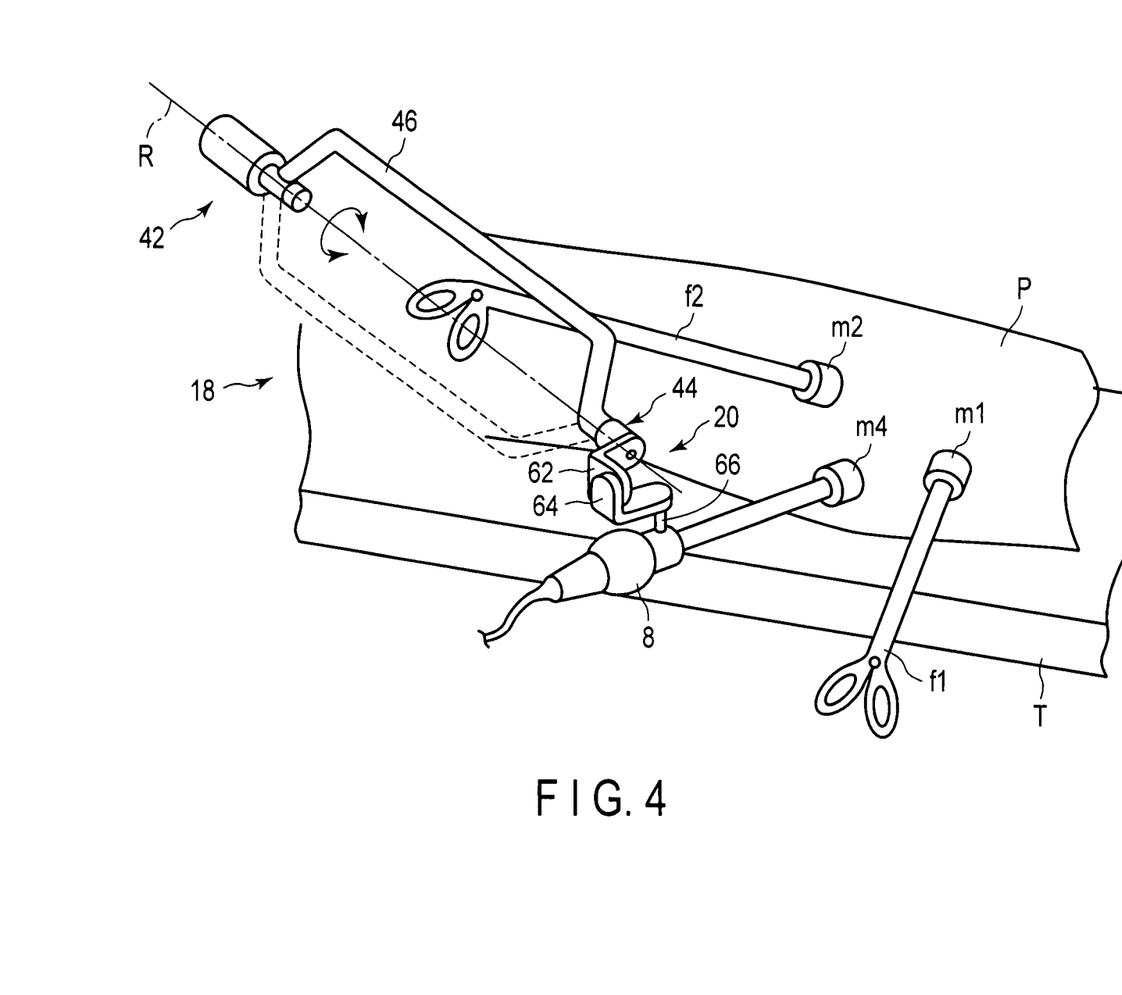
FIG. 4 is an enlarged view illustrating a main part in FIG. 3.

Hereinafter, preferred embodiments will be described with reference to the drawings. FIG. 1 is a view illustrating an entire configuration of a supporting apparatus used for medical treatment according to a first embodiment. FIG. 2 is a view illustrating a detailed configuration of a coupling unit of a support arm and a moving arm of the supporting apparatus used for medical treatment in FIG. 1. FIG. 3 is a view illustrating a situation of an operation in which the supporting apparatus used for medical treatment in FIG. 1 is used. FIG. 4 is an enlarged view illustrating a main part in FIG. 3.

A supporting apparatus used for medical treatment 10 is disposed in clinical rooms, such as an operating room, an examining room, and a treatment room, and supports medical observation apparatuses, such as a microscope and an endoscope. A position of the supporting apparatus used for medical treatment 10 can freely be moved in a three-dimensional space irrespective of a surrounding environment, whereby a medical apparatus function of the supporting apparatus used for medical treatment 10 is sufficiently exerted and a feeling of fatigue provided to operators, such as a doctor, is reduced as much as possible.

As illustrated in FIG. 1, the supporting apparatus used for medical treatment 10 includes a moving arm 16, which is supported by a base unit 12 placed on a floor F of the clinical room with a support post unit 14 interposed therebetween. A support arm 18 is coupled to one end side of the moving arm 16. An endoscope 8 that is of the medical observation apparatus is attached to a supporting unit 20 coupled to a leading end side of the support arm 18. The endoscope 8 is vertically and horizontally freely moved by the support post unit 14 and the moving arm 16 together with the supporting unit 20, and the endoscope 8 is stable supported at a desired position.

The base unit 12 is formed into a block or plate-like structure so as to be able to move along the floor F using plural casters 12a disposed on a bottom surface side. The support post 14 extends toward from an upper surface side of the base unit 12, and can turn about a vertical axis line O1. Braking means or fixing means may be provided in the base unit 12 in order to prevent rotations of the casters 12a or to prevent the base unit 12 from moving on the floor F.

The support post 14 extends upward along the vertical axis line O1 from the base unit 12, and the support post 14 supports the moving arm 16 on an upper end side thereof while the moving arm 16 turns freely about a horizontal axis line O2. In the support post 14, the turning about the vertical axis O1 with respect to the base unit 12 is regulated by a braking device B1. For example, the support post 14 fixed by the braking device B1 can be released by stepping on a manipulation switch b provided in a foot switch W.

The moving arm 16 is supported on the leading end side of the support post 14. A link mechanism unit 22 constituting a parallelogram link mechanism is provided in the moving arm 16.

The link mechanism unit 22 includes an upper link 24, a lower link 26, a coupling link 28, and a revolving link 30. The upper link 24 and the lower link 26 are disposed in a plane orthogonal to the horizontal axis O2 and in parallel with each other. The revolving link 30 is supported on an upper end side of the support post 14 while being able to revolve about the horizontal axis O2.

Therefore, the link mechanism unit 22 can freely turn about the horizontal axis O2 in a plane perpendicular to the horizontal axis O2. A braking device B2 regulates the rotation of the link mechanism unit 22 about the horizontal axis O2. The fixing of the revolving link 30 is released by the braking device B2, which allows the moving arm 16 to turn to the desired position about the horizontal axis O2. Similarly the braking device B2 can be actuated through a manipulation switch (not illustrated) provided in the foot switch W.

In the embodiments, the words of "upper" and "lower" are used only in the description with reference to the drawings, but do not indicate an absolute positional relationship. The same holds true for the words of "inner" and "outer" and "front" and "rear".

The link mechanism unit 22 includes a rotation axis C1 of a joint 32, a rotation axis C2 of a joint 34, a rotation axis C3 of a joint 36, and a rotation axis C4 of a joint 38. The four rotation axes are disposed in parallel with the horizontal axis O2. The joint 32 turnably couples the upper link 24 to the revolving link 30. The joint 34 turnably couples the upper link 24 to the coupling link 28. The joint 36 turnably couples the lower link 26 to the coupling link 28. The joint 38 turnably couples the lower link 26 to the revolving link 30.

In the embodiment, a braking device B3 is provided in the joint 32. The braking device B3 releases the braking to turn the links about the four rotation axes C1 to C4 of the link mechanism unit 22. The pair of the upper link 24 and the lower link 26, which is located opposite each other, and the pair of the coupling link 28 and the revolving link 30, which is located opposite each other, is translated by the turning, thereby deforming the quadrangular shape of the four links. A manipulation switch (not illustrated) for the braking device B3 of the link mechanism unit 22 may be provided in the foot switch W.

A base end side of the support arm 18 is coupled to a front portion on the upper end side of the moving arm 16. For example, the supporting device 20 having three degrees of freedom is coupled to the leading end side of the support arm 18. The supporting device 20 supports the endoscope 8.

A balance weight unit 40 is attached to a rear portion on the lower end side of the moving arm 16. The balance weight unit 40 cancels rotation moment that is generated about the horizontal axis O2. Accordingly, even if the braking devices B2 and B3 are released, the endoscope 8 supported by the supporting device 20 can be supported at the desired position.

In the embodiment, the support arm 18 is provided on an extended line of the upper link 24. The balance weight unit 40 is disposed in the lower link 26 that moves in the direction orthogonal to the vertical axis O1 and the horizontal axis O2. For example, the balance weight unit 40 can be changed according to a weight of the medical observation apparatus 8, and the position of the balance weight unit 40 can be changed.

The support arm 18 of the embodiment includes a base-end-side coupling unit 42 that is rotatable coupled to the upper link 24 and a leading-end-side coupling unit 44 that is rotatably coupled to the supporting unit 20. An offset unit 46 that is laterally offset is disposed between the leading-end-side coupling unit 44 and the base-end-side coupling unit 42.

The base-end-side coupling unit 42 and the leading-end-side coupling unit 44 are disposed on an axis line R. The offset unit 46 extends in substantially parallel with the axis line R while being laterally offset from the axis line R. One end of the offset unit 46 is coupled to the base-end-side coupling unit 42 with an inner arm unit 45 interposed therebetween, and the other end is coupled to the leading-end-side coupling unit 44 with the outer arm unit 47 interposed therebetween.

Preferably the axis line R extends so as to be orthogonal to the rotation axes C1 and C2 on the upper side of the moving arm 16. In this case, when the offset unit 46 is turned, the gravity center of the whole of the supporting apparatus used for medical treatment 10 can easily be loaded on the vertical axis line O1.

The axis line R in FIG. 1 is disposed in coaxial with a line connecting the rotation axes C1 and C2. However, the axis line R is not necessarily disposed in coaxial with the line connecting the rotation axes C1 and C2. The offset unit 46 may be disposed in the direction of the line connecting the rotation axes C1 and C2, or the offset unit 46 may be disposed so as to extend in parallel with the line connecting the rotation axes C1 and C2.

As illustrated in FIG. 2, the base-end-side coupling unit 42 has a structure in which a ring unit 45a provided in a base portion of the inner arm unit 45 is rotatably attached onto a short axis 24a extending from the upper link 24. In the embodiment, a semi-fixed unit 48 is provided on the leading end side of the base-end-side coupling unit 42 formed by the ring unit 45a and the short axis 24a. The semi-fixed unit 48 can support the support arm 18 in a semi-fixed state with respect to the upper link 24 of the moving arm 16, namely, the semi-fixed unit 48 can support the offset unit 46 of the support arm 18 at any rotation position by a frictional force. A force larger than the frictional force is applied to the offset unit 46, which allows the support arm 18 to immediately turn to be reallocated at the desired position.

In the semi-fixed unit 48, a nut-shaped presser ring 50 is engaged with a screw formed at a leading end of the short axis 24a, and a disc spring 54 is disposed between two washers 52a and 52b. The semi-fixed unit 48 moves the presser ring 50 along the axis line R to adjust the frictional force between the inner arm unit 45 and the upper link 24.

When the presser ring 50 is screwed in the side of the upper link 24, a biasing force of the disc spring 54 increases to increase the frictional force between the upper link 24 and the inner arm unit 45. On the other hand, the frictional force decreases when the presser ring 50 is screwed off. The offset unit 46 can be supported at a proper position by properly adjusting the frictional force. The frictional force may be adjusted according to the biasing force by increasing and decreasing the number of disc springs 54 of the semi-fixed unit 48, for example, by increasing the number of disc springs 54 from one to four.

The leading-end-side coupling unit 44 can similarly be formed. In this case, preferably a short axis is provided in a main body unit 60 (see FIG. 1) of the supporting unit 20, and rotatably fitted in a ring unit 47a of the outer arm unit 47. In each case, center axes of the ring units 45a and 47a are disposed on the axis line R passing through the base-end-side coupling unit 42 and the leading-end-side coupling unit 44, which allows only the offset unit 46 to be smoothly turned without changing the position of the endoscope 8.

As illustrated in FIG. 1, the supporting unit 20 includes the main body unit 60 that constitutes the leading-end-side coupling unit 44 together with the ring unit 47a of the outer arm unit 47. Two L-shape tilt links 62 and 64 are turnably coupled to the main body unit 60 to form the three-degree-of-freedom supporting unit 20.

In the embodiment, one of leg portions of the tilt link 62 is coupled so as to be turnable about a first rotation axis K1. One of leg portions of the tilt link 64 is coupled to the other leg portion of the tilt link 62 so as to be turnable about a second turning axis K2. A grip link 66 supporting the endoscope 8 is coupled to the other leg portion of the tilt link 64 so as to be turnable about a third rotation axis K3.

The first, second, and third rotation axes K1, K2, and K3 are orthogonal to one another like the well-known X, Y, and Z axes. Preferably the first rotation axis K1 is coaxial with the axis line R that is of the rotation axis of the support arm 18. Therefore, the position and attitude of the endoscope 8 supported by the supporting unit 20 do not change even if the offset unit 46 of the support arm 18 is turned about the axis line R.

Particularly, in the case that the gravity center of a total of the endoscope 8 and the supporting device. 20 is located below the axis line R and the first rotation axis K1, the position and the attitude of the endoscope 8 supported by the supporting unit 20 do not change when he whole of the supporting apparatus used for medical treatment 10 is rotated about the third rotation axis K3.

FIGS. 3 and 4 illustrate an example of an intraperitoneal surgery using the endoscope 8 that is of a laparoscope. For example, ports m1, m2, and m3 are formed in a patient P on an operating bed T using a trocar. Forceps f1, f2, and f3 are inserted in the patient P through the ports m1, m2, and m3. The endoscope 8 is inserted through an observation port m4 in order to observe an intraperitoneal situation.

An imaging device (not illustrated) that captures an observation image is provided at the leading end of the endoscope 8. The observation image observed with the endoscope 8 is displayed on a main-side monitor M1 and an assistant-side monitor M2 through a camera control unit connected to the imaging device.

In the case that the operation is performed using the endoscope 8, an operator S moves the base unit 12 of the supporting apparatus used for medical treatment 10 using the caster 12a of the base unit 12, and positions the supporting apparatus used for medical treatment 10 at a required position. Then the operator S steps the switch b of the foot switch W to release the braking of the braking devices B1, B2, and B3, and the operator S moves the endoscope 8 supported by the supporting unit 20. After inserting the endoscope 8 in the observation port m4, the operator S actuates the braking devices B1, B2, and B3 to fix the support post 14 and the moving arm 16 with respect to the base unit 12, thereby fixing the movement of the link mechanism unit 22.

The operator S also inserts the forceps f1 and f2 in the ports m1 and m2, and an assistant D inserts the forceps f3 in the port m3.

The operator S and the assistant D view a video image and perform a required treatment. The video image is captured by the endoscope 8 connected to a camera control unit (not illustrated), and displayed on the monitors M1 and M2 disposed on front surface sides of the operator S and the assistant D.

Under the situation of the operation in FIG. 4, sometimes the forceps f2 manipulated by the operator S interferes with the support arm 18. When the forceps f2 interferes with the support arm 18, the operator S can rotate the offset unit 46 of the support arm 18 about the axis line R from a solid-line position in FIG. 4 and move the offset unit 46 to a broken-line position. Therefore, a work space necessary for the operation can be ensured.

In rotating the offset unit 46 of the support arm 18, the support arm 18 is rotatably coupled to the leading-end-side coupling unit 44 and the base-end-side coupling unit 42 while supporting the supporting unit 20 and the moving arm 16 in the same attitudes in the three-dimensional space. Therefore, even if the offset unit 46 is rotated, the position and the attitude of the endoscope 8 do not change, and an observation visual field of the endoscope 8 does not change.

Because the support arm 18 in which the supporting unit 20 is coupled to the leading end side thereof can rotate the offset unit 46 with respect to both the supporting unit 20 and the moving arm 16, the supporting apparatus used for medical treatment 10 can be moved while the interference between the support arm 18 and the operator S and the assistant S or peripheral devices, such as the forceps f2 is avoided, and the work space can easily be ensured without changing the position at which the whole of the supporting apparatus used for medical treatment 10 is placed.

The position at which the supporting apparatus used for medical treatment 10 is placed is not limited to one, but a degree of freedom is obtained in the position at which the supporting apparatus used for medical treatment 10 is placed irrespective of the relationship with the observation port m4. Accordingly, even in the narrow operating space, the necessary work space can be ensured by the extremely simple configuration of the support arm 18 of the supporting apparatus used for medical treatment 10.

Figure 5:
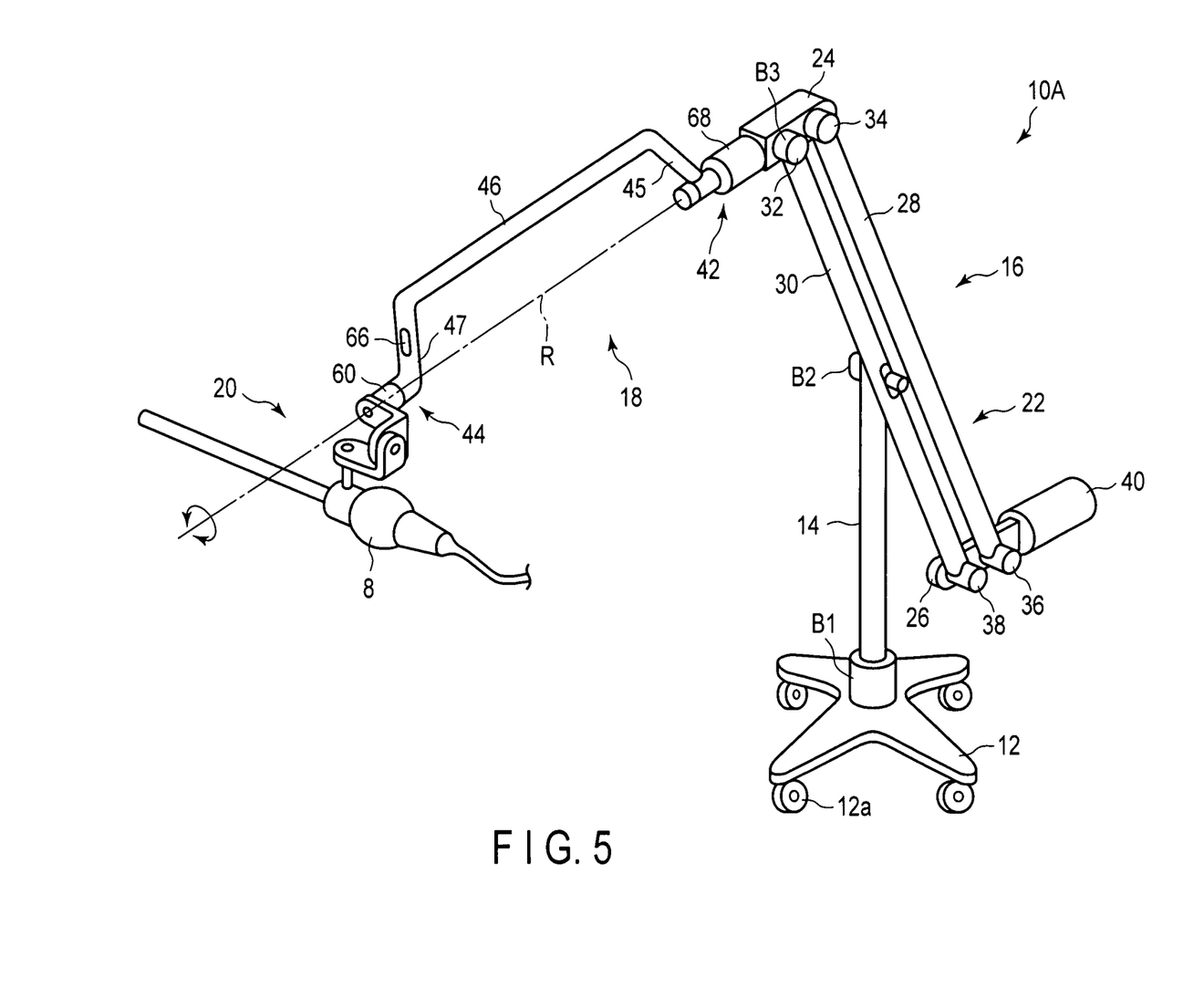
FIG. 5 is a view illustrating an entire configuration of a supporting apparatus used for medical treatment according to a second embodiment.
Figure 6:
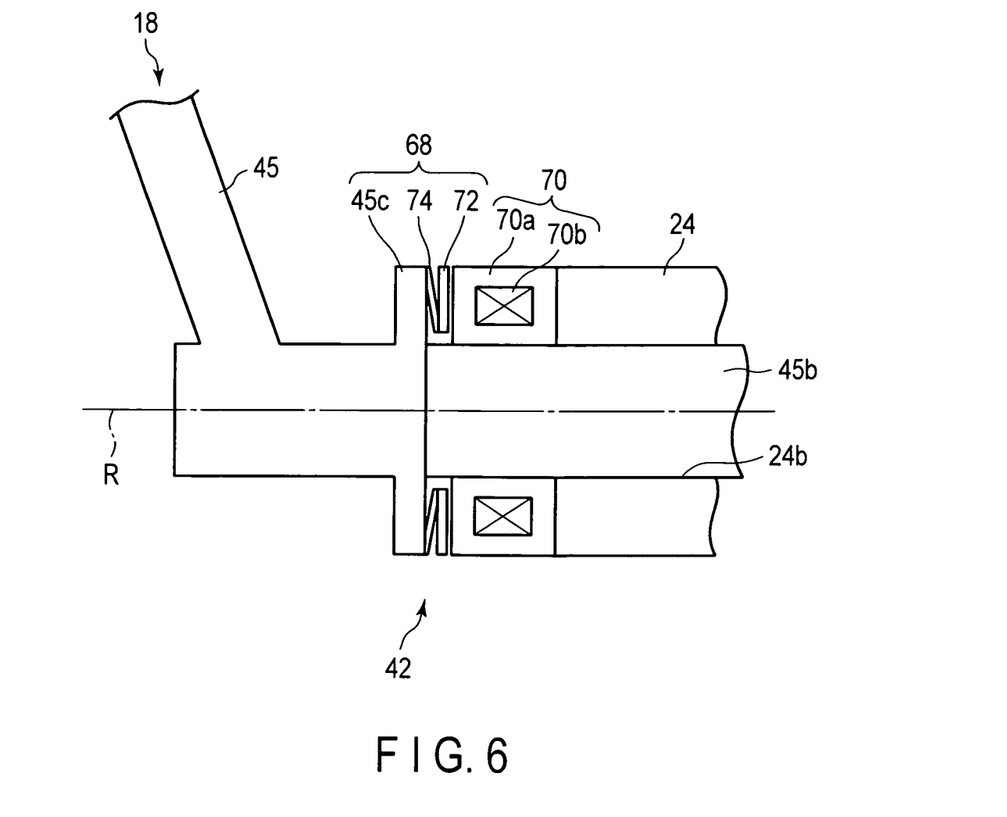
FIG. 6 is a view illustrating a detailed configuration of a coupling unit of a support arm and a moving arm of the supporting apparatus used for medical treatment in FIG. 5.

FIGS. 5 and 6 illustrate a supporting apparatus used for medical treatment 10A according to another embodiment. The following embodiments and modifications are basically identical to the above embodiment. Therefore, the same component is designated by the same sign, and the detailed description is omitted.

In a supporting apparatus used for medical treatment 10A of another embodiment, a braking device 68 is provided in the base-end-side coupling unit 42 as regulating means for regulating the rotation of the offset unit 46 of the support arm 18, and a brake releasing switch 66 is provided in the outer arm unit 47 as regulation releasing means for selectively releasing the rotation regulation of the offset unit 46 by the braking device 68.

As illustrated in FIG. 6, an inner hole 24b coaxial with the axis line R is made forward in the upper link 24 of the moving arm 16. A shaft unit 45b, which is projected backward and fitted in the inner hole 24b of the upper link 24, and a flange 45c in which a diameter is larger than that of the inner hole 24b are formed at base end of the inner arm unit 45 of the support arm 18.

A ring stator 70, an armature 72, and a plate spring 74 are disposed between an opening end of the upper link 24 and the flange 45c of the inner arm unit 45 to constitute the braking device 68.

The stator 70 includes a core member 70a that is constructed by a permanent magnet fixed to the upper link 24 and an electromagnet coil 70b that is connected to a controller (not illustrated) to generate a magnetic force canceling a magnetic force of the core member 70a during energization of the electromagnet coil 70b. The energization of the electromagnet coil 70b is controlled by a switch 66 (see FIG. 5) disposed in the outer arm unit 47. Usually, the electromagnet coil 70b is not energized, but the stator 70 attracts the armature 72 and the flange 45c using the magnetic force of the core member 70a, and supports the upper link 24 and the inner arm unit 45 in the integrally fixed state.

In the case that the offset unit 46 of the support arm 18 is turned, the operator S supports the support arm 18 at the proper position, and presses the switch 66 to energize the electromagnet coil 70b of the stator 70. Therefore, the magnetic force of the core member 70a is canceled, and the plate spring 74 separates the armature 72 from the stator 70 to release the fixing by the braking device 68. The shaft unit 45b of the inner arm unit 45 is released from the upper link 24.

According to the supporting apparatus used for medical treatment 10A having the above support arm 18, the offset unit 46 can securely be fixed. Additionally, the switch 66 is provided in the outer arm unit 47 in order to release the braking device 68, so that the manipulation of the switch 66 and the turning of the offset unit 46 can simultaneously be performed.

When the operator S releases the a pressing force of the switch 66 after turning the offset unit 46 of the support arm 18 to the necessary position, the magnetic force is returned in the stator 70 to actuate the braking device 68.

Figure 7:
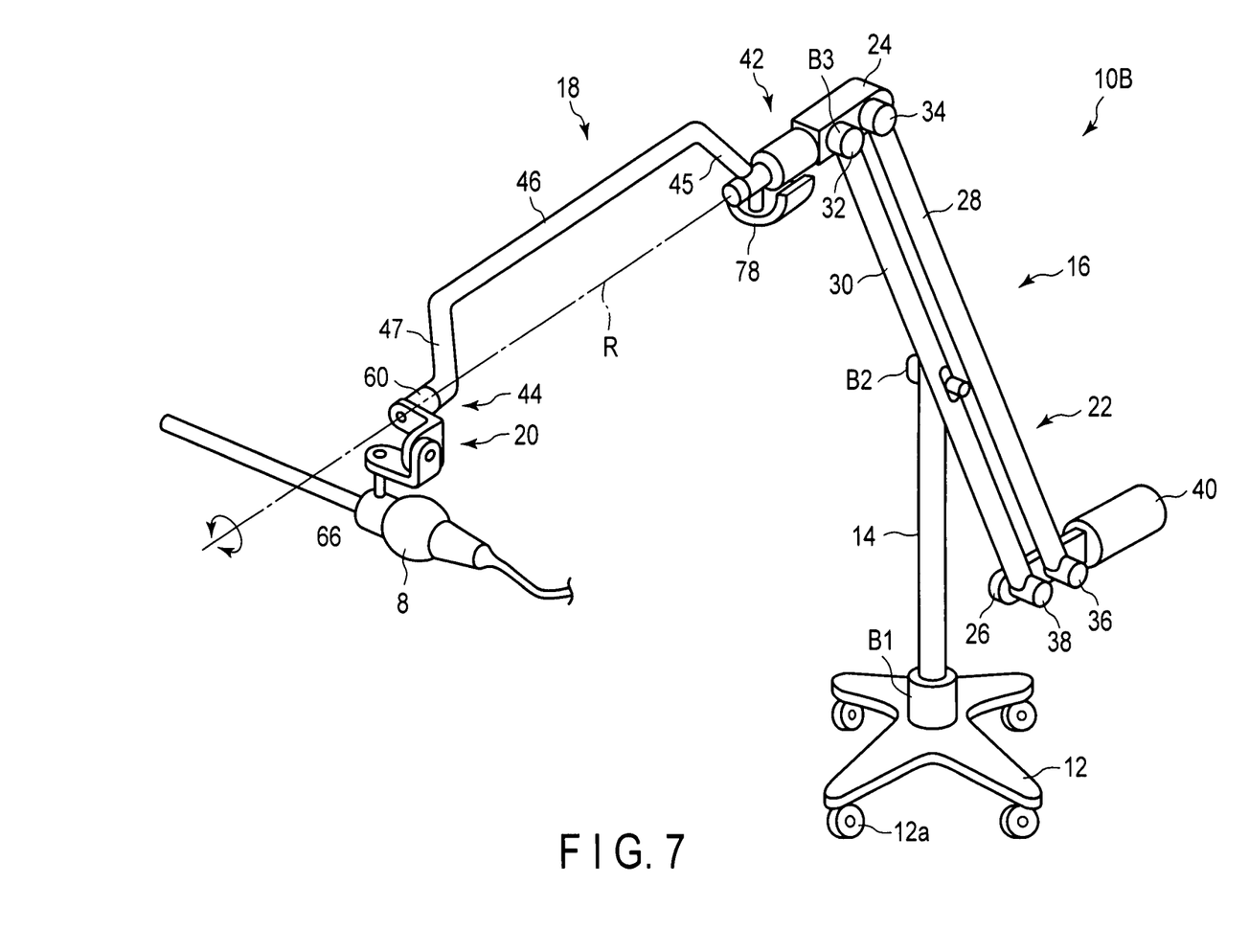
FIG. 7 is a view illustrating an entire configuration of a supporting apparatus used for medical treatment according to a third embodiment.

FIG. 7 illustrates a supporting apparatus used for medical treatment 10B in which a weight compensating weight unit 78 is provided in the support arm 18.

For example, the weight unit 78 is fixed to a base portion of the inner arm unit 45. Preferably the weight unit 78 has a rotation radius and a weight, which cancel the rotation moment of the offset unit 46, the inner arm unit 45, and the outer arm unit 47 about the axis line R. As illustrated in FIG. 7, a compact structure can be implemented by forming the weight unit 78 into a semi-cylindrical shape with the axis line R as the center.

In the supporting apparatus used for medical treatment 10B, when the offset unit 46 rotates about the axis line R, the weight unit 78 also rotates in conjunction with the offset unit 46. The gravity center of the whole of the support arm 18 is disposed on the axis line R, which allows the offset unit 46 to be rotated with an extremely light force.

Therefore, even if the support arm 18 is rotated about the axis line R, the gravity center position is always located on the axis line R. Because the gravity center position does not move from the axis line R, an imbalance of the support arm 18 is not generated. The support arm 18 can be manipulated with a light force during the manipulation of the leading-end-side endoscope 8.

Figure 8A:
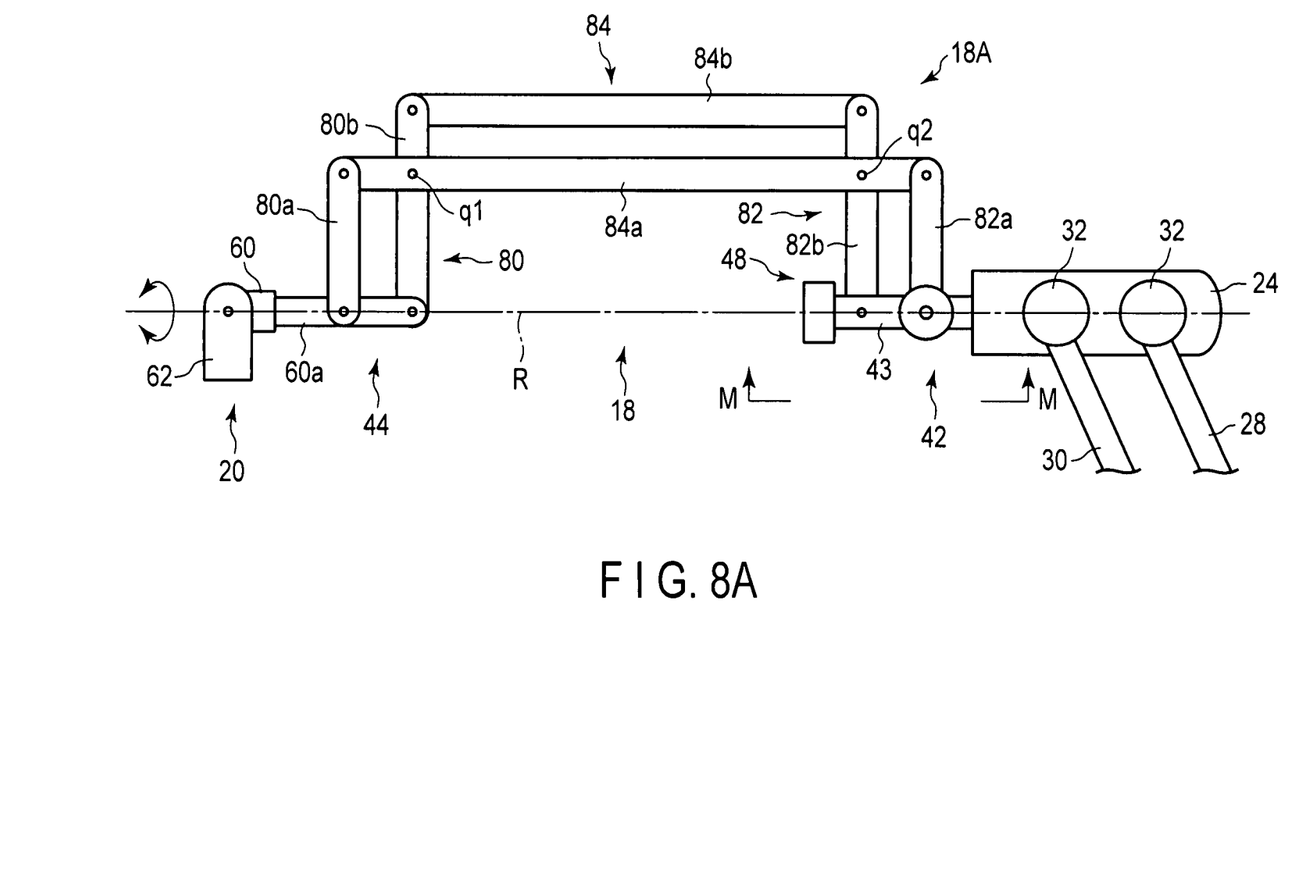
FIG. 8A is a view illustrating a configuration of a first modification of the support arm.
Figure 8B:
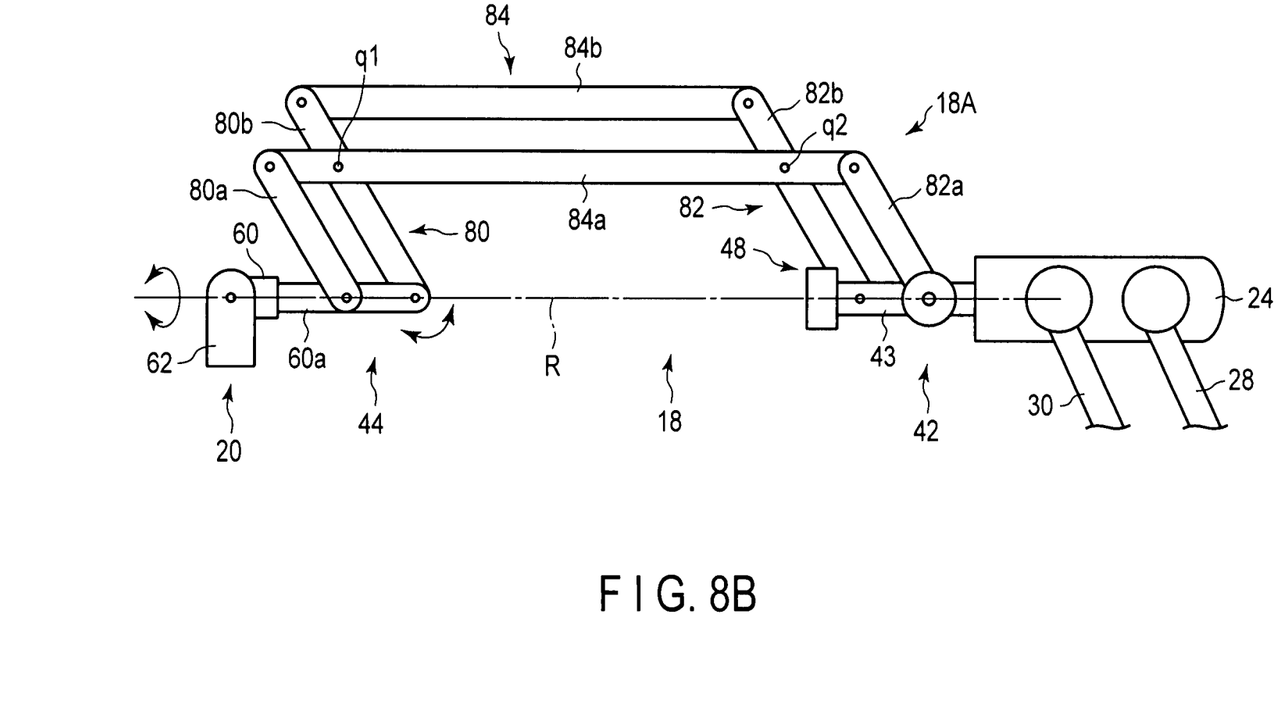
FIG. 8B is a view illustrating a state in which the support arm in FIG. 8A is operated.
Figure 9:
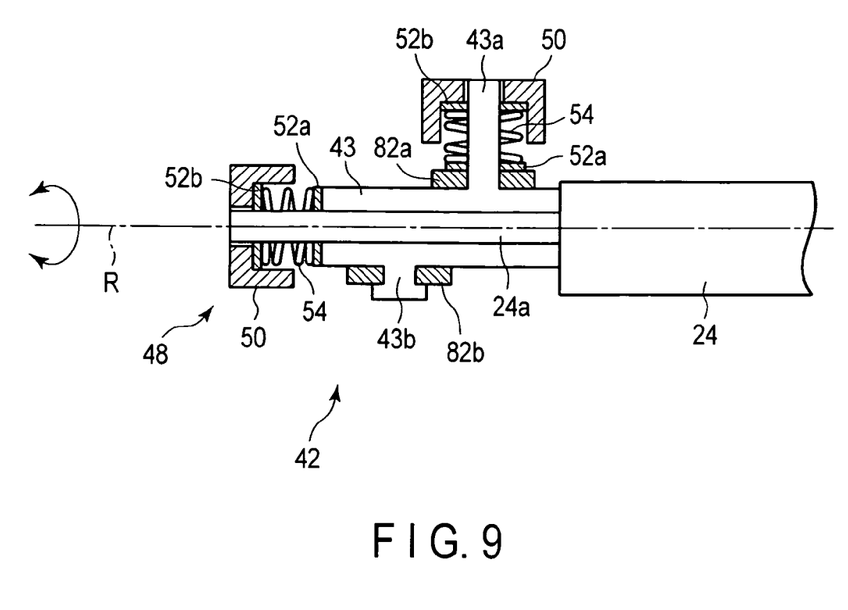
FIG. 9 is a view illustrating a sectional configuration taken on a line M-M in FIG. 8A.

FIGS. 8 and 9 illustrate a support arm 18A according to a modification.

The support arm 18A is formed as a parallelogram link mechanism. In the embodiment, each of an outer arm unit 80, an inner arm unit 82, and an offset unit 84 is also formed by the parallelogram link mechanism, and the outer arm unit 80, the inner arm unit 82, and the offset unit 84 are interlocked by coupling the outer arm unit 80, the inner arm unit 82, and the offset unit 84 to one another.

As illustrated in FIG. 8, the outer arm unit 80 is constructed by two outer link members 80a and 80b, which are disposed about the axis line R and along the axis line R and are parallel to each other. Similarly, the inner arm unit 82 is constructed by two outer link members 82a and 82b, which are disposed along the axis line R and are parallel to each other. The offset unit 84 is constructed by two offset link members 84a and 84b that are disposed in parallel with the axis line R.

One end side of each of the outer link members 80a and 80b is pivoted in a shaft unit 60a, which is attached to the main body unit 60 of the supporting unit 20 while being turnable about the axis line R, and the other end side is pivoted in each of the offset link members 84a and 84b. One end side of each of the inner link members 82a and 82b is attached to a cylindrical base member 43, which is turnably attached to the short axis 24a projected forward from the upper link 24. The other end side is pivoted in each of the offset link members 84a and 84b.

In the drawings, the outer link member 80a, the inner link member 82a, and the offset link member 84a, to which the sign a is added, and the outer link member 80b, the inner link member 82b, and the offset link member 84b, to which the sign b is added, are disposed across the axis line R from each other. The offset link member 84a is coupled to the outer link member 80b and the inner link member 82b while being turnable about turning axes q1 and q2. Therefore, the parallelogram link mechanisms of the outer arm unit 80, the inner arm unit 82, and the offset unit 84 can move in conjunction with one another.

As illustrated in FIG. 9, one end side of each of the inner link members 82a and 82b is pivoted in the cylindrical base member 43. One end of the inner link member 82b is turnably attached to a radially-projected shaft 43b. One end of the inner link member 82a is turnably attached to the projected shaft 43b. A front end of the base member 43 is supported in the semi-fixed state onto the short axis 24a by the semi-fixed unit 48, and the rotation position about the axis line R is supported. The inner link member 82a is also supported in the semi-fixed state on the projected shaft 43a by the similar semi-fixed means, and a tilt position of the inner link member 82a can be supported.

According to the support arm 18A, the outer arm unit 80 and the inner arm unit 82 can move from the state in which the outer arm unit 80 and the inner arm unit 82 are disposed perpendicular to the axis line R as illustrated in FIG. 8A to the state in which the outer arm unit 80 and the inner arm unit 82 are tilted with respect to the axis line R as illustrated in FIG. 8B. At this point, the semi-fixed means 54 supports the inner link member 82b in the semi-fixed state, so that the outer arm unit 80 and the inner arm unit 82 can be tilted on the opposite side to the state in FIG. 8B. In both the disposition states, a distance between the supporting unit 20 and the upper link 24 does not vary but is kept constant.

For example, in the case that the forceps 2 in FIG. 4 interferes with the outer arm unit 80 of the support arm 18A, the outer arm unit 80 and the inner arm unit 82 are tilted with respect to the axis line R, and the parallelogram is broken by one of the outer link members 80a and 80b of the outer arm unit 80. Therefore, the forceps 2 and the outer arm unit 80 can be disposed at the positions at which the forceps 2 does not interfere with the outer arm unit 80.

In the support arm 18A, each of the outer arm unit 80, the inner arm unit 82, and the offset unit 84 is formed by two link members, three parallelogram link mechanisms are formed, and 10 turning axes parallel to one another are provided as a whole. Alternatively, at least one of the outer arm unit 80, the inner arm unit 82, and the offset unit 84 may be formed by one link member.

In this case, for example, the movements of the outer arm unit 80, the inner arm unit 82, and the offset unit 84 can be interlocked by use of interlocking means (not illustrated), such as a timing belt. In this case, the number of components can be decreased because at least three link members may be required. Therefore, the total of four turning axes, namely, a turning axis about which one end side of the outer arm unit 80 rotates with respect to the supporting unit 20, a turning axis about which one end side of the inner arm unit 82 rotates with respect to the base member 43, two turning axes about which the other end side of each of the outer arm unit 80 and the inner arm unit 82 rotates with respect to the offset unit 84 are disposed in parallel, which allows the outer arm unit 80 and the inner arm unit 82 to freely turn with respect to the axis line R to prevent the interference.

Figure 10:
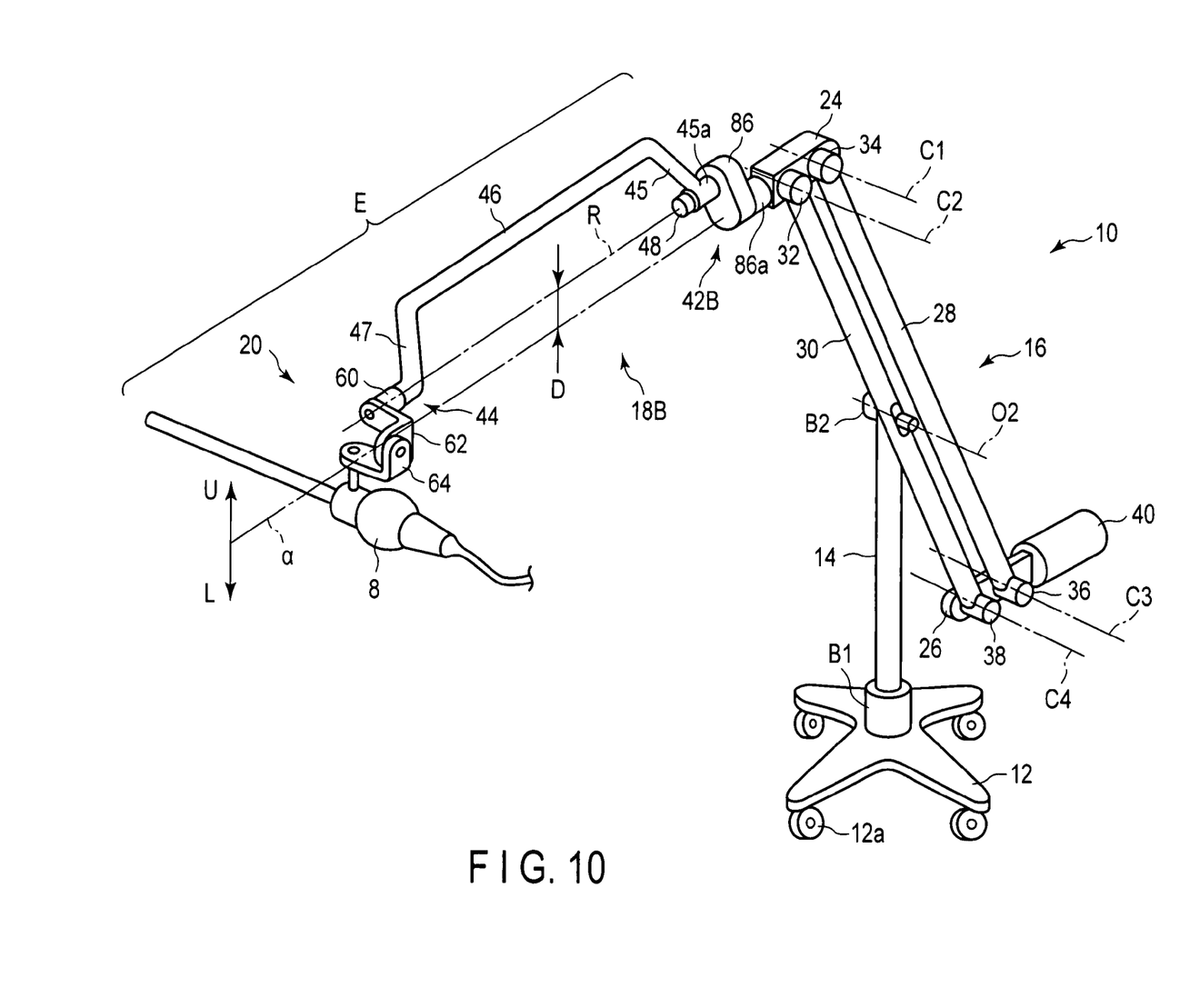
FIG. 10 is a view illustrating a configuration of a second modification of the support arm.

FIG. 10 illustrates the supporting apparatus used for medical treatment 10 including a support arm 18B according to another modification.

The support arm 18B includes an offset arm 86 in which a base-end-side coupling unit 42B is bent into a crank shape. The support arm 18B is coupled to the upper link 24 of the moving arm 16 by the offset arm 86.

The offset arm 86 in FIG. 10 includes a coupling shaft 86a that is coupled to the upper link 24 of the moving arm 16 on the base end side, and the inner arm unit 45 is attached onto the leading end side of the offset arm 86. The coupling shaft 86a passes through an axis line α, which is orthogonal to the two rotation axes C1 and C2 of the moving arm 16, and fixed to the upper link 24.

A bias D between the axis line α and the axis line R is adjusted such that the gravity center of a leading-end-side portion E from the offset arm 86 is disposed on the axis line α. Specifically, a portion including the support arm 18B, the supporting unit 20, and the endoscope 8 is adjusted such that the weight of a portion of upward direction U above the axis line α is equal to the weight of a portion of downward direction L above the axis line α. Therefore, the gravity center of the leading-end-side portion E from the offset arm 86 is disposed on the axis line α.

The balance weight unit 40 can be balanced by disposing the gravity center of the portion E on the axis line α, and the gravity center of the total of the moving arm 16, the support arm 18B, the supporting unit 20, and the endoscope 8 can be disposed on the horizontal axis line O2 to implement the complete balanced state.

Because the support arm 18B is included, like the embodiment in FIG. 1, the offset unit 46 can be actuated about the axis line R to obtain the complete balanced state on the support post 14. Therefore, operability of the support arm 18B and the supporting unit 20 is further improved.

In the support arm 18B, the axis line α is disposed in parallel with the axis line R, the offset arm 86 does not rotate, but the offset unit 46 can rotate about the axis line R. In the support arm 18B, the inner arm unit 45 may be constructed by the link member that can be tilted with respect to the axis line R or the axis line α as illustrated in FIGS. 8 and 9. The position can finely be adjusted by tilting the inner arm unit 45.

The supporting apparatus used for medical treatment is described as the medical observation apparatus in association with the endoscope. The supporting apparatus used for medical treatment is not limited to the medical observation apparatuses, such as the endoscope, but the supporting apparatus used for medical treatment can support various medical apparatuses, such as a medical display device and a medical treatment device. The medical observation apparatus is not limited to the laparoscope, but the supporting apparatus used for medical treatment can support endoscopes for brain surgery and gynecology.

According to the supporting apparatus used for medical treatment of the embodiments of the invention, in the support arm in which the supporting unit is coupled to the leading end side, the offset unit can rotate with respect to both the supporting unit and the moving arm. Therefore, the supporting apparatus used for medical treatment can move while the interference between the upper arm and the operator and the assistant or peripheral devices, such as the forceps, is avoided, the work space can easily be ensured without changing the position at which the whole apparatus is placed and the attitude of the portion except the offset unit, and the degree of freedom is obtained in disposition of the supporting apparatus used for medical treatment.

The supporting unit has the three degrees of freedom to tilt the medical observation apparatus, and the first rotation axis constituting one of the three degrees of freedom is disposed in coaxial with the axis line passing through the leading-end-side coupling unit and the base-end-side coupling unit of the support arm. In such cases, even if the offset unit of the support arm is rotated, the other two degrees of freedom are not affected.

At this point, when the gravity center of the total of the supporting unit and the medical observation apparatus is disposed below the rotation axis that is coaxial with the axis line passing through the leading-end-side coupling unit and the base-end-side coupling unit of the support arm, even if the offset unit of the support arm is rotated, the attitude of the medical observation apparatus is maintained.

In the case that the base-end-side coupling unit includes the semi-fixed means for supporting the rotation of the support arm with respect to the moving arm in the semi-fixed state, the support arm can be supported at any rotation position.

In the case that the regulation means for regulating the rotation of the support arm with respect to the moving arm and the regulation releasing means for selectively releasing the regulation of the regulation means are included, the support arm is securely fixed to the desired position to prevent the unintentional rotation, and the support arm can be rotated only in the necessary case.

The supporting unit has the three degrees of freedom, the supporting unit includes the first rotation axis that is disposed in coaxial with the axis line passing through the leading-end-side coupling unit and the base-end-side coupling unit of the support arm, the second rotation axis that is disposed perpendicular to the first rotation axis and disposed along the observation optical axis of the medical observation apparatus supported by the supporting unit, and the third rotation axis that is disposed perpendicular to the second rotation axis and disposed perpendicular to the observation optical axis, and the medical observation apparatus is tilted about the first, second, and third rotation axes. In such cases, when the offset unit of the support arm is rotated, the degree of freedom of the supporting device is not obstructed, but the medical observation apparatus can be supported at the desired position while the required attitude is maintained.

In the case that the support arm includes the weight compensating unit that cancels the rotation moment of the offset unit about the axis line, the imbalance state of the support arm is not generated, but the support arm can be manipulated with the light force during the manipulation of the medical observation apparatus. In the case that the support arm includes at least three link members in which four rotation axes, which are disposed perpendicular to the axis line and are parallel to one another, constitute four vertices of the parallelogram, the support arm can be deformed by relatively moving the three link members, and the interference can more effectively be prevented.

The above embodiments and modifications can be combined in various ways. For example, in the case that the support arm 18A in FIGS. 8 and 9 that can be deformed or the support arm 18B including the offset arm 86 in FIG. 10 is used, the braking device 68 in FIGS. 5 and 6 or the weight unit 78 in FIG. 7 may be provided.

According to the embodiment of the invention, the supporting apparatus used for medical treatment that can easily ensure the work space without changing the position at which the whole apparatus including the base unit or the base is placed and have the degree of freedom in the disposition.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A supporting apparatus used for medical treatment comprising:
    a pair of coupling units comprising a first coupling unit and a second coupling unit, the pair of coupling units being is turnably provided while separated from each other by a predetermined distance on a first rotation axis, the first rotation axis defining a longitudinal axis;
    a turning arm unit which includes a first end portion and a second end portion, the turning arm unit extending in a longitudinal direction and being formed in a U-shape, the turning arm unit being laterally separated from the first rotation axis by a U-shaped curve and a predetermined distance;
    a pair of arm units comprising a first arm unit and a second arm unit, in which the pair of coupling units and the first end portion and the second end portion of the turning arm unit are coupled such that the turning arm unit can turn about the first rotation axis while a predetermined interval is maintained;
    a moving arm unit which is coupled to a first coupling unit of the pair of coupling units while being turnable about the first rotation axis, the moving arm unit supporting the turning arm unit such that the turning arm unit can move vertically and horizontally;
    a first tilt link which includes a leading end portion and a base end portion, the base end portion being coupled to the second coupling unit of the pair of coupling units while the base end portion is turnable about the first rotation axis;
    a second tilt link which is coupled to the leading end portion of the first tilt link while being turnable about a second rotation axis having a direction different from that of the first rotation axis; and
    a supporting unit which is coupled to the second tilt link while being turnable about a third rotation axis having a direction different from that of the first and second rotation axes, the supporting unit supporting a medical observation apparatus,
    wherein, when the turning arm unit is turned about the first rotation axis, the medical observation apparatus being supported by the supporting unit does not change in position and attitude.

2. The supporting apparatus used for medical treatment according to claim 1, wherein a gravity center of a total of the supporting unit, the second coupling unit of the pair of coupling units, the first tilt link, the second tilt link, and the medical observation apparatus is disposed below the first rotation axis when the supporting unit supports the medical observation apparatus.

3. The supporting apparatus used for medical treatment according to claim 1, wherein the first coupling unit comprises a semi-fixed unit that is capable of supporting the turning arm unit at any turning position with respect to the moving arm unit.

4. The supporting apparatus used for medical treatment according to claim 1, further comprising:
    braking device for regulating the turning of the turning arm unit with respect to the moving arm unit; and
    brake releasing switch for selectively releasing regulation of the braking device.

5. The supporting apparatus used for medical treatment according to claim 2, wherein the first, second, and third rotation axes are disposed such that each of the first, second, and third rotation axes is perpendicular to other rotation axes, and the medical observation apparatus is tilted about the first, second, and third rotation axes.

6. The supporting apparatus used for medical treatment according to claim 1, wherein a base end portion of the first arm unit includes a weight compensating unit that cancels rotation moment between the turning arm unit and the pair of arm units about the first rotation axis.

7. The supporting apparatus used for medical treatment according to claim 1, wherein the first end portion and the second end portion of the turning arm unit and the pair of arm units are disposed in a radial direction with respect to the first rotation axis and are coupled to each other by parallel fourth and fifth rotation axes, and the pair of arm units and the pair of coupling units are coupled to each other by sixth and seventh rotation axes parallel to the fourth and fifth rotation axes, in a manner that the turning arm unit and the pair of arm units form three sides of a parallelogram.

8. A supporting apparatus used for medical treatment comprising:
- a pair of coupling units comprising a first coupling unit and a second coupling unit, the pair of coupling units being is turnably provided while separated from each other by a predetermined distance on a first rotation axis, the first rotation axis defining a longitudinal axis;
- a turning arm unit which includes a first end portion and a second end portion, the turning arm unit extending in a longitudinal direction while being laterally separated from the first rotation axis by a predetermined distance;
- a pair of arm units comprising a first arm unit and a second arm unit, in which the pair of coupling units and the first end portion and the second end portion of the turning arm unit are coupled such that the turning arm unit can turn about the first rotation axis and rotate 360 degrees while a predetermined interval is maintained;
- a moving arm unit which is coupled to a first coupling unit of the pair of coupling units while being turnable about the first rotation axis, the moving arm unit supporting the turning arm unit such that the turning arm unit can move vertically and horizontally;
- a first tilt link which includes a leading end portion and a base end portion, the base end portion being coupled to the second coupling unit of the pair of coupling units while the base end portion is turnable about the first rotation axis;
- a second tilt link which is coupled to the leading end portion of the first tilt link while being turnable about a second rotation axis having a direction different from that of the first rotation axis; and
- a supporting unit which is coupled to the second tilt link while being turnable about a third rotation axis having a direction different from that of the first and second rotation axes, the supporting unit supporting a medical observation apparatus,
- wherein, when the turning arm unit is turned about the first rotation axis, the medical observation apparatus being supported by the supporting unit does not change in position and attitude.

* * * * *